US008657771B2

(12) United States Patent
Weaver, II et al.

(10) Patent No.: US 8,657,771 B2
(45) Date of Patent: Feb. 25, 2014

(54) ORTHOPEDIC DEVICE FOR STABILIZING THE THUMB

(75) Inventors: Edward Leonard Weaver, II, Milford, OH (US); Sherry Ann Hinds, Goshen, OH (US)

(73) Assignee: 3M Innovative Properties Company, St. Paul, MN (US)

( * ) Notice: Subject to any disclaimer, the term of this patent is extended or adjusted under 35 U.S.C. 154(b) by 2620 days.

(21) Appl. No.: 10/409,308

(22) Filed: Apr. 8, 2003

(65) Prior Publication Data

US 2003/0191421 A1    Oct. 9, 2003

Related U.S. Application Data

(60) Provisional application No. 60/370,851, filed on Apr. 8, 2002.

(51) Int. Cl.
*A61F 5/00* (2006.01)

(52) U.S. Cl.
USPC .................................. 602/20; 602/21; 602/22

(58) Field of Classification Search
USPC ........... 602/20–22; 128/878–880; 482/44, 47; 2/159, 161.1, 161.4, 162, 166–168
See application file for complete search history.

(56) References Cited

U.S. PATENT DOCUMENTS

| | | | |
|---|---|---|---|
| 1,607,208 A | 11/1926 | Pease | |
| 2,271,927 A | 2/1942 | Saighman | |
| 3,265,064 A | 8/1966 | Gruber | |
| 3,586,001 A | 6/1971 | Sanderson | |
| 3,598,408 A | 8/1971 | Klose | |
| 3,789,842 A | 2/1974 | Froimson | |
| 3,815,908 A | 6/1974 | Hashimoto | |
| 3,877,426 A | 4/1975 | Nirschl | |
| 3,926,186 A | 12/1975 | Nirschl | |
| 3,942,525 A | 3/1976 | Dragan | |
| 3,970,081 A | 7/1976 | Applegate, Jr. | |
| D242,172 S | 11/1976 | Borenstein et al. | |
| 4,014,327 A | 3/1977 | Spiro | |
| 4,047,250 A | 9/1977 | Norman | |
| 4,048,991 A | 9/1977 | Marx | |
| 4,128,097 A | 12/1978 | Bilinsky et al. | |
| 4,182,318 A | 1/1980 | Beige et al. | |
| 4,228,548 A | 10/1980 | Cohen | |
| 4,243,028 A | 1/1981 | Puyana | |
| 4,273,130 A | 6/1981 | Simpson | |
| 4,323,232 A | 4/1982 | Terpening | |
| 4,354,280 A | 10/1982 | Hayes | |
| 4,519,097 A | 5/1985 | Chappell, Jr. et al. | |

(Continued)

FOREIGN PATENT DOCUMENTS

WO    WO 02/094140 A2    11/2002

OTHER PUBLICATIONS

MODABBER™; Hely & Weber Innovative Supports, www.hely-weber.com; © 1999 Weber Orthopedic Inc DBA Hely & Weber.

*Primary Examiner* — Michael A. Brown
(74) *Attorney, Agent, or Firm* — Kevin W. Weber

(57) ABSTRACT

An orthopedic device for stabilizing the thumb, i.e. a thumb support. The orthopedic device is worn by a user to stabilize the thumb for treatment of hand and thumb injuries. The device is capable of being worn on either the right hand or left hand of a user and has one or more metal stays made from soft metal material and have an ergonomic design to contour to the hand and thumb.

53 Claims, 5 Drawing Sheets

(56) References Cited

U.S. PATENT DOCUMENTS

| | | | |
|---|---|---|---|
| 4,531,241 A | 7/1985 | Berger | |
| 4,584,993 A | 4/1986 | Nelson | |
| 4,632,105 A | 12/1986 | Barlow | |
| 4,658,441 A | 4/1987 | Smith | |
| 4,854,309 A * | 8/1989 | Elsey | 602/21 |
| D310,738 S | 9/1990 | Brown | |
| 5,014,689 A | 5/1991 | Meunchen et al. | |
| 5,063,613 A | 11/1991 | Brown | |
| 5,267,943 A | 12/1993 | Dancyger | |
| 5,497,510 A | 3/1996 | Knowles et al. | |
| D368,351 S | 4/1996 | Yewer, Jr. | |
| 5,513,657 A * | 5/1996 | Nelson | 128/879 |
| 5,526,531 A | 6/1996 | Olson et al. | |
| 5,538,501 A | 7/1996 | Caswell | |
| D378,148 S | 2/1997 | Haney | |
| 5,649,900 A * | 7/1997 | Kline | 602/21 |
| 5,682,611 A | 11/1997 | Kline | |
| 5,728,059 A * | 3/1998 | Wiesemann et al. | 602/64 |
| 5,787,896 A | 8/1998 | Sackett | |
| 5,819,313 A | 10/1998 | McCrane | |
| 5,873,130 A | 2/1999 | Lafferty | |
| 5,899,870 A | 5/1999 | Deirmendjian et al. | |
| 5,928,172 A * | 7/1999 | Gaylord | 602/21 |
| 5,933,868 A | 8/1999 | Bender | |
| 5,963,985 A | 10/1999 | Behr et al. | |
| D416,650 S | 11/1999 | Stevens | |
| 5,983,408 A | 11/1999 | Li | |
| 5,987,641 A | 11/1999 | Walker | |
| 5,997,495 A | 12/1999 | Cook et al. | |
| 6,013,044 A | 1/2000 | Estwanik | |
| 6,024,715 A * | 2/2000 | Maxwell | 602/64 |
| 6,093,165 A | 7/2000 | Estwanik | |
| 6,101,628 A | 8/2000 | Earl | |
| 6,142,966 A | 11/2000 | Hely | |
| 6,146,348 A | 11/2000 | Slautterback | |
| 6,186,969 B1 | 2/2001 | Bell et al. | |
| 6,190,344 B1 * | 2/2001 | Bobroff | 602/21 |
| 6,195,803 B1 | 3/2001 | Russell et al. | |
| 6,196,985 B1 | 3/2001 | Slautterback | |
| 6,199,211 B1 | 3/2001 | Franzolino | |
| 6,200,286 B1 | 3/2001 | Zamani | |
| 6,219,843 B1 | 4/2001 | Passi et al. | |
| 6,261,252 B1 | 7/2001 | Darcey | |
| 6,269,487 B1 | 8/2001 | Schryver et al. | |

\* cited by examiner

ORTHOPEDIC DEVICE FOR STABILIZING THE THUMB

CROSS REFERENCE TO RELATED APPLICATION

This application claims the priority of U.S. Provisional Patent Application No. 60/370,851 filed Apr. 8, 2002, which is incorporated herein by reference.

BACKGROUND OF THE INVENTION

The invention pertains to an orthopedic device for stabilizing the thumb, i.e. a thumb support. The thumb support is worn by a user to stabilize the thumb for treatment of hand and thumb injuries.

Thumb injuries may occur in chronic and acute forms from a range of activities. For instance, chronic thumb injuries may result from repetitive work tasks, such as gripping hand tools used in an assembly line operation. Overuse of the thumb, accompanied by the loads and vibrations from the use of the hand tools, can result in persistent thumb pain. Acute injuries can occur in sports activities and can include sprains or fractures resulting from an abrupt impact of the thumb on an object or other person.

Conventional devices for supporting the thumb typically involve the use of a soft, flexible sleeve material that extends around the wrist and hand and wraps around the thumb. Such flexible sleeve materials often provide insufficient support to promote healing of an acutely injured thumb, or prevent further injury of a chronically injured thumb. Other conventional devices include the use of a rigid stay that is held to the thumb using the flexible material. The rigid stay, however, can be uncomfortable to wear.

Therefore, it would be advantageous to have a thumb support that is comfortable to wear while still providing adequate support to promote healing and/or prevent further injury.

SUMMARY OF THE INVENTION

An orthopedic device for stabilizing the thumb of one embodiment of the present invention generally comprises first and second sheets of material each having outer and inner surfaces, and right, left, distal and lateral edges. The sheets of material are attached together along the right edges.

The distal edges of the first and second sheets each comprise an extended element having an opening to accommodate the thumb of a user. The extended elements are about adjacent to the right edges and arcuate sections of the distal edges. The arcuate sections are concave with respect to the distal edges and conform substantially to the web in the medial of the hand between the thumb and the adjoining digit. The distal edges substantially along a plane from arcuate sections to the lateral edges, and the lateral edges, define a hand opening such that the thumb support is substantially a sleeve open on one side that can be worn on and releaseably secured to either the right hand or left hand of a user.

The thumb support may comprise at least one stay member made of soft metal material that is shaped to follow the contour of the sleeve and right edges of the first and second sheets. The stay members allow a user to customize the stay members to meet individual needs and comfort and have ergonomic design to contour to the hand and thumb, which provides natural thumb positioning. The stay members can be removeably inserted into elongated sleeves located on the outer surfaces of the first and second sheets proximate to the right edges of each sheet. Each elongated sleeve is defined by a piece of material secured at its periphery, such as by stitching, to the respective outer surface of the first sheet and second sheet and comprise a slit at about the bottom of the piece of material (e.g. near the lateral edge) that allows a user to removeably insert one or more stay members into each elongated sleeve.

The thumb support also comprises a wrist strap secured at one end to the left edge of the second sheet and secured at the other end to a wrist strap securing portion. The wrist strap comprises a two part fastening system. A tab having one portion of a two part fastening system may be secured to the left edge of the second sheet by the same attachment means used to secure the wrist strap to the second sheet. A mating portion of the fastening system of the tab is attached to the outer surface of the first sheet about adjacent to the elongated sleeve and the left edge. In use, a user will place the thumb into the opening of the extended elements and then secure the tab to the mating portion thus releaseably securing the first sheet and second sheet to the palmar and dorsal side of the hand and wrist, and then the user can releaseably adjust the tension on the wrist by wrapping the wrist strap against itself and engaging the two part fastening system of the wrist strap.

The thumb support may further comprise a thumb strap secured at one end to the extended element on the outer surface of the second sheet and at the other end to a thumb strap securing portion. The thumb strap comprises a two part fastening system and in use can be wrapped around and releaseably secured to itself.

DETAILED DESCRIPTION OF THE INVENTION

Figure 1:
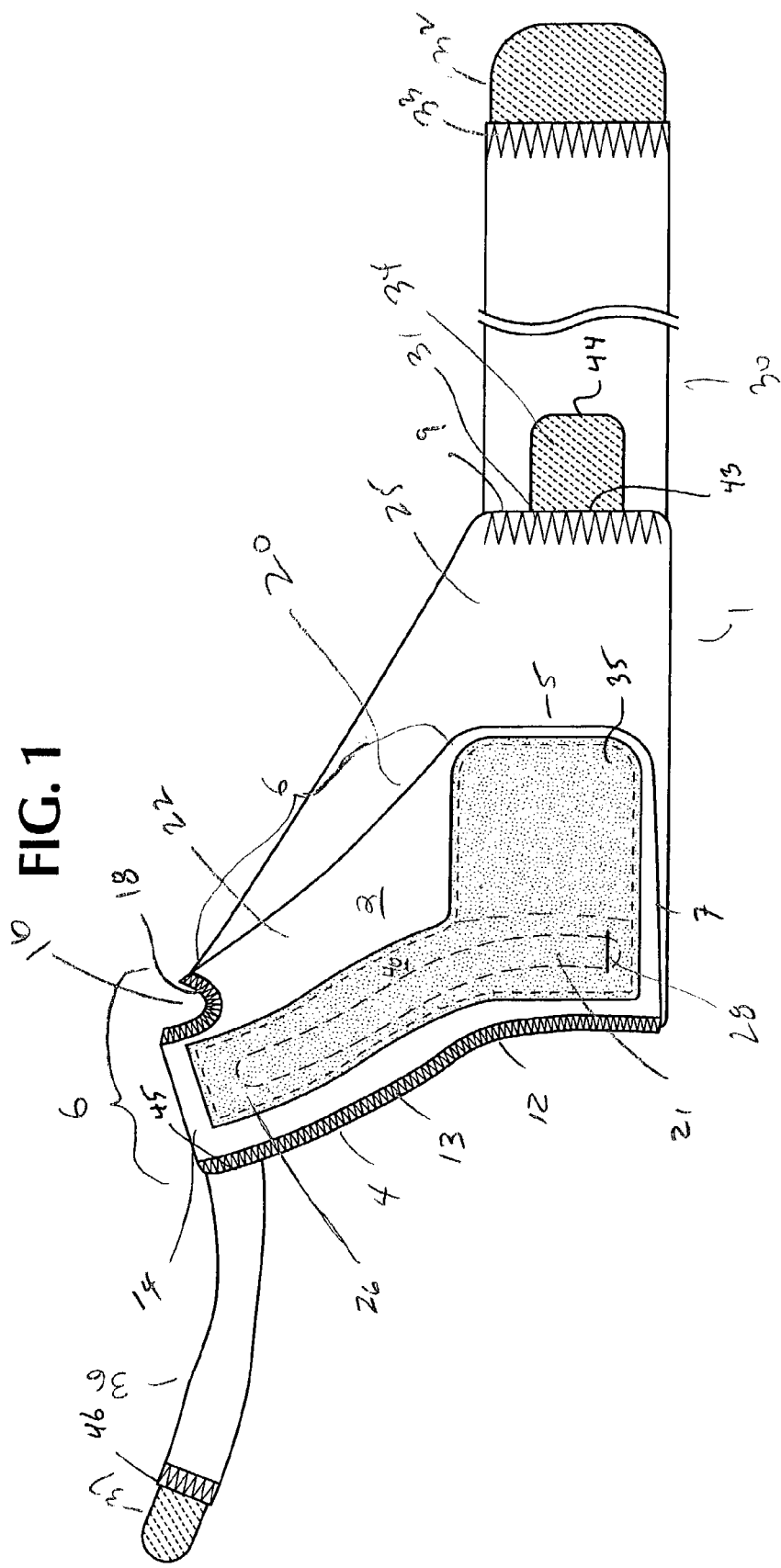
FIG. 1 is a front view of an orthopedic device for stabilizing the thumb in accordance with an embodiment of the invention.
Figure 2:
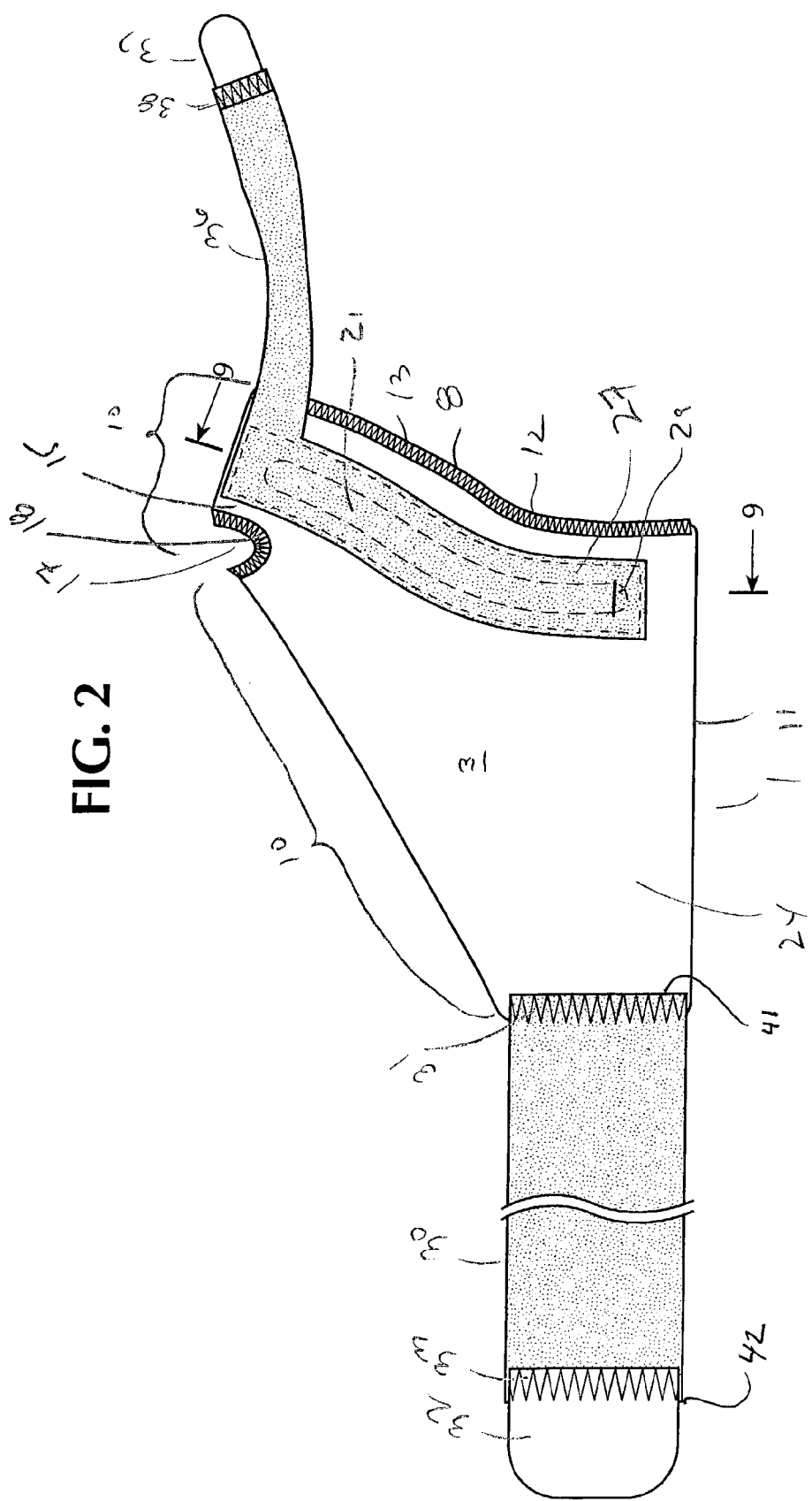
FIG. 2 is a back view of an orthopedic device for stabilizing the thumb in accordance with an embodiment of the invention.

Referring now to FIGS. 1 and 2, the orthopedic device for stabilizing the thumb, i.e. thumb support, 1 comprises a first sheet 2 and a second sheet 3 of material preferably having elasticity and breathability. These sheets can be made from any textile or other material suitable for use in orthopedic supports, for example neoprene. Preferably, however, the first sheet 2 and second sheet 3 are made from open cell urethane foam, which has better breathability than other materials, including neoprene. S-1203 hypercell open cell urethane foam available from Rubberlite, Huntington, W. Va., USA may be used in the invention. The first sheet 2 is generally smaller than the second sheet 3, but need not be smaller.

Again referring to FIGS. 1 and 2, the first sheet has an outer surface 22 and an inner surface 23 and a right edge 4, left edge 5, distal edge 6 and lateral edge 7. The second sheet 3 has an outer surface 24 and an inner surface 25 and a right edge 8, left edge 9, distal edge 10 and lateral edge 11. The right edges (4, 8) of the first sheet 2 and second sheet 3 are curvilinear having an arch or kink 12 at about the midpoint of the edges such that the right edges (4, 8) are shaped to substantially conform to the outer contour of the radial of the hand from about the wrist to about metacarpophalangeal joint of the thumb. The right edges (4, 8) of the first sheet 2 and second sheet 3 are attached together by first attachment means 13, such as Radio Frequency welding (RF Welding), stitching, adhesives, and the like, and combinations thereof, preferably as shown in the figures, stitching.

The distal edges (6, 10) of the first sheet 2 and second sheet 3 each comprise an extended element (the first extended element designated 14 for the first sheet 2 and the second extended element designated 15 for the second sheet 3) about adjacent to the right edges (4, 8). The distal edges (6, 10) further comprise arcuate sections (the first arcuate section designated 16 for the first sheet 2 and the second arcuate section designated 17 for the second sheet 3). The arcuate sections (16, 17) are concave with respect to the distal edges (6, 10) of the first sheet 2 and second sheet 3 and the arcuate sections conform substantially to the web in the medial of the hand between the thumb and the adjoining digit. The arcuate sections (16, 17) are attached together by second attachment means 18 such as Radio Frequency welding (RF Welding), stitching, adhesives, and the like, and combinations thereof, preferably as shown in the figures, stitching. The distal edges (6, 10) extend substantially along a plane from the right edges (4, 8) to the arcuate sections (16, 17) so as to define a thumb opening 19. The distal edges (6, 10) extend substantially along a plane from the arcuate sections (16, 17) to the lateral edges (7, 11) and the lateral edges (7, 11) so as to define a hand opening 20 such that the thumb support is substantially an open sleeve that can be worn on and releaseably secured to either the right hand or left hand of a user.

Figure 7:
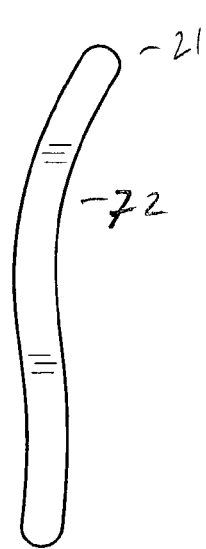
FIG. 7 is a stay member which can be inserted into an elongated sleeve of an orthopedic device for stabilizing the thumb in accordance with an embodiment of the invention.
Figure 8:
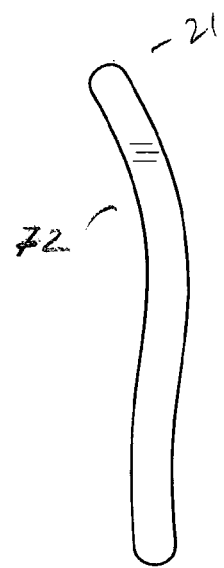
FIG. 8 is a stay member which can be inserted into an elongated sleeve of an orthopedic device for stabilizing the thumb in accordance with an embodiment of the invention.

The thumb support preferably comprises at least one stay member, most preferably at least one stay member 21 on each side of the thumb, as shown in FIGS. 1 and 2. The stay members 21 are shown in FIGS. 7 and 8. Each stay member 21 has a stay member arch or kink 72. The stay members 21 are made of soft metal material and can be shaped to follow the contour of the sleeve and left edges of the first and second sheets. The stay members allow a user to customize the stay members to meet individual needs and comfort and have ergonomic design to contour to the hand and thumb, which provides natural thumb positioning.

The stay members 21 can be removeably inserted into a first elongated sleeve 26 on the outer surface 22 of the first sheet 2 and a second elongated sleeve 27 on the outer surface 24 of the second sheet 3. The first elongated sleeve 26 and second elongated sleeve 27 are proximate to the right edges (4, 8) located on opposite sides of the first sheet 2 and second sheet 3. The elongated sleeves follow the contour of the right edges (4, 8) of the sheets from about the opening for the thumb 14 to the lateral edges (7, 11). Each elongated sleeve is defined by a piece of material (39, 40) secured at its periphery, such as by stitching, to the respective outer surface (22, 24) of the first sheet 2 and second sheet 3. Each elongated sleeve comprises a slit (28, 29) at about the bottom of the piece of material (e.g. near the lateral edge).

The elongated sleeves (26, 27) can accommodate one or more stay members 21, and in a preferred embodiment of the invention each elongated sleeve (26, 27) comprises at least one stay member 21 such that in use at least one stay member is along the dorsal side of the thumb and at least one stay member is along the palmar side of the thumb. In use, the stay members 21 can be removeably inserted into one or both elongated sleeves (26, 27). The material that defines the elongated sleeve may be any type of material, such as textile material, and may also be a laminate such as a laminate comprising one portion of a hook and loop type fastener like VELCRO®, such as that available from Velcro USA Inc., Manchester, N.H., USA.

As shown in FIGS. 1 and 2, the orthopedic device for stabilizing the thumb also comprises a wrist strap 30 having a first end 41 and a second end 42 which is attached at one end, (e.g. the first end 41) to the left edge 9 of the second sheet 3 by third attachment means 31, such as Radio Frequency welding (RF Welding), stitching, adhesives, and the like, and combinations thereof, preferably as shown in the figures, stitching, and is secured at the other end, (e.g. the second end 42) to a wrist strap securing portion 32 by fourth attachment means 33, such as Radio Frequency welding (RF Welding), stitching, adhesives, and the like, and combinations thereof, preferably as shown in the figures, stitching. The wrist strap 30 can be made from material that is hook engageable for full-length adjustability. The wrist strap securing portion 32 is generally the loop portion of a hook and loop type fastener, such as that available from Velcro USA Inc. In use, the securing portion 32 can be releaseably secured to the wrist strap 30, by the preferred means of a hook and loop type fastener, however, it should be understood that any type of fastening system can be employed without departing from the scope of the invention, such as snaps, buttons, belts, straps and the like.

Figure 3:
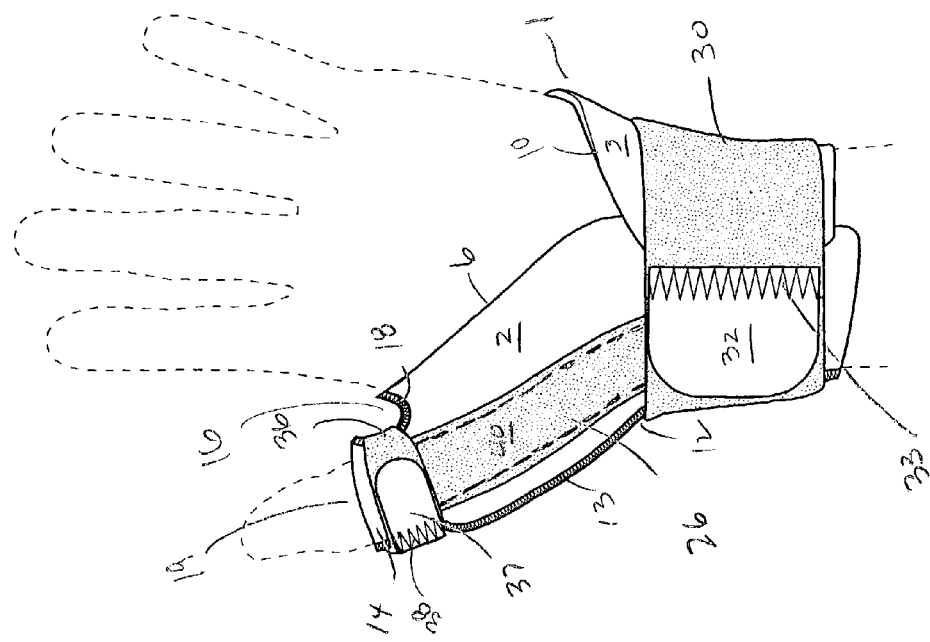
Figure 6:
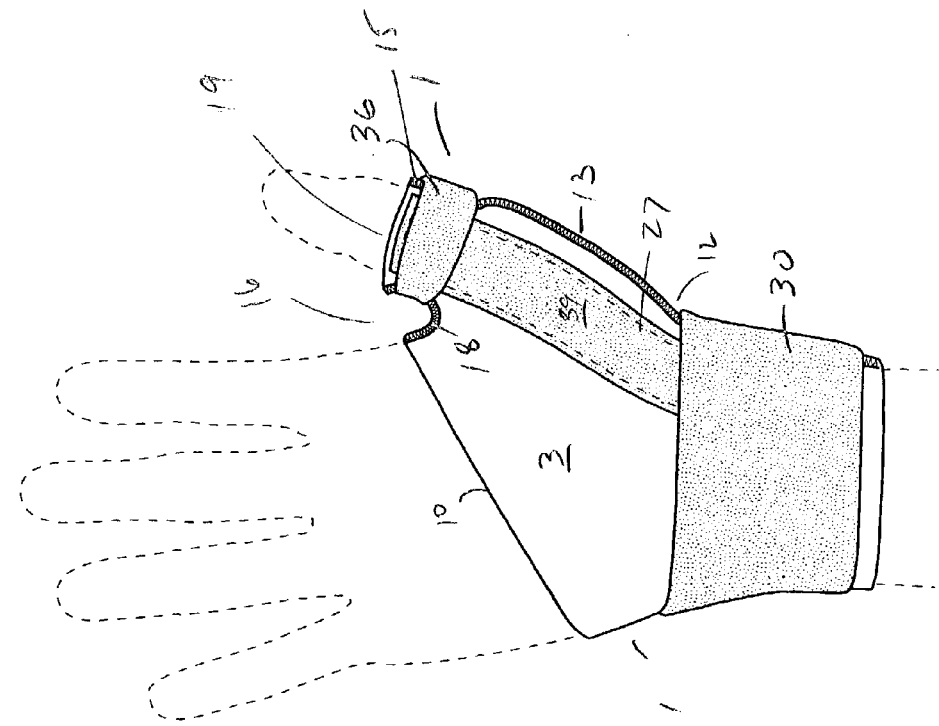
FIGS. 5 and 6 are perspective views of an orthopedic device for stabilizing the thumb in accordance with an embodiment of the invention worn on the left hand of a user.

As shown in FIGS. 2 and 3, the thumb support may also comprise a tab 34 having a first end 43 and a second end 44 preferably made from the hook portion of a hook and loop type fastening system that may be attached at the first end 43 to the left edge 9 of the second sheet 3 by the third attachment means 31. A mating portion 35 of this fastening system, preferably the loop portion of a hook and loop type fastening system, is attached to the outer surface 22 of the first sheet 2 about adjacent to the elongated sleeve 26 and the left edge 5. The mating portion 35 is preferably made from the same material that defines the elongated sleeve 26. In use, the tab 34 can be releaseably secured to the mating portion 35, by the preferred means of a hook and loop type fastener, however, it should be understood that any type of fastening system can be employed without departing from the scope of the invention, such as snaps, buttons, belts, straps and the like. The tab 34 allows the user to more easily apply the needed compression with the wrist strap 30.

The thumb support may further comprise a thumb strap 36 having a first end 45 and a second end 46 as shown in FIGS. 1 and 2. The thumb strap 36 is attached at one end, (e.g. the first end 45) to the extended element 15 on the outer surface 24 of the second sheet 3, preferably attached by the same stitching that secures the material defining the elongated sleeve to the outer surface 24, and is attached at the other end, (e.g. the second end 46) to a thumb strap securing portion 37 by fifth attachment means 38, such as Radio Frequency welding (RF Welding), stitching, adhesives, and the like, and combinations thereof, preferably as shown in the figures, stitching. The thumb strap 36 can be made from material that is hook engageable for full-length adjustability. The thumb strap securing portion 37 is generally the loop portion of a hook and loop type fastener, such as that available from Velcro USA Inc. In use the thumb strap securing portion 37 can be releaseably secured to the thumb strap 36, by the preferred means of a hook and loop type fastener, however, it should be understood that any type of fastening system can be employed without departing from the scope of the invention, such as snaps, buttons, belts, straps and the like. The thumb strap 36 can be wrapped around the extended elements (14, 15) about adjacent to the distal edges (6, 10), and releaseably secured to itself using the two part fastening system. The thumb strap 36 allows the user to vary compression around the thumb for personal needs and comfort, provides additional support to the thumb and allows a user with a smaller thumb size to gain the benefit of full support that may not be available from the extended elements without applying the thumb strap.

Figure 4:
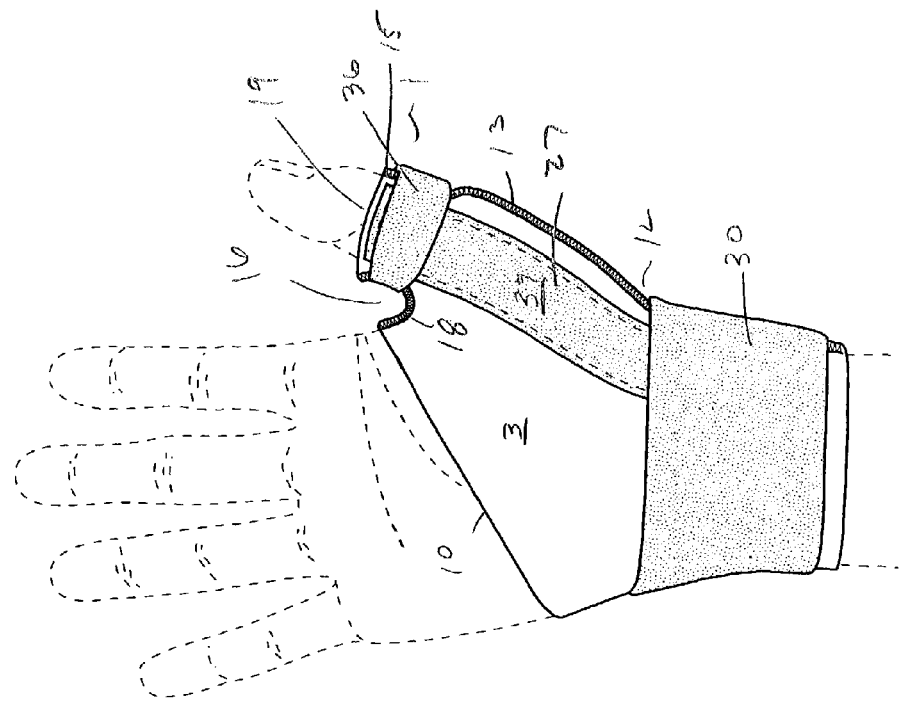
FIGS. 3 and 4 are perspective views of an orthopedic device for stabilizing the thumb in accordance with an embodiment of the invention worn on the right hand of a user.
Figure 5:
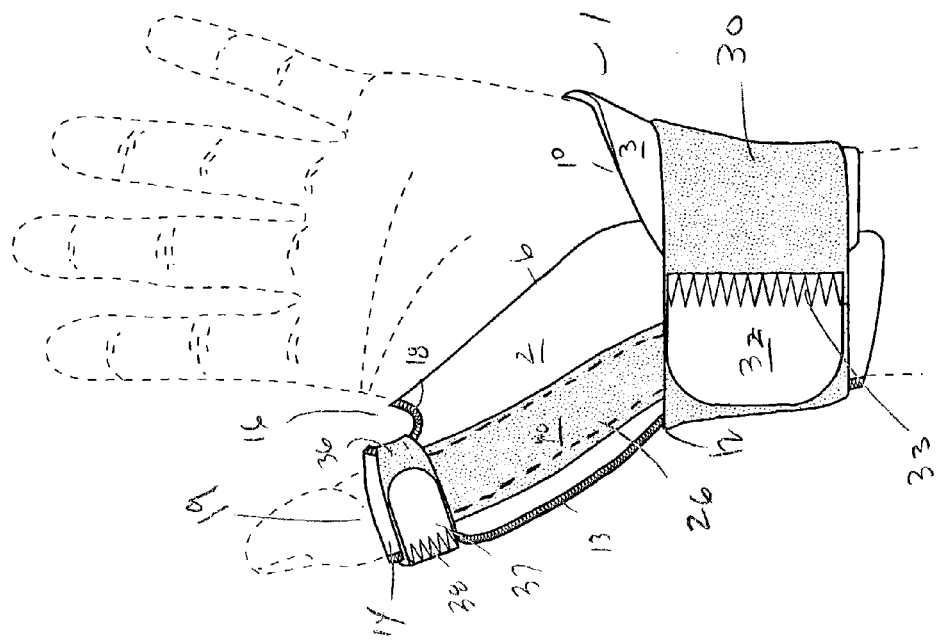
Figure 9:
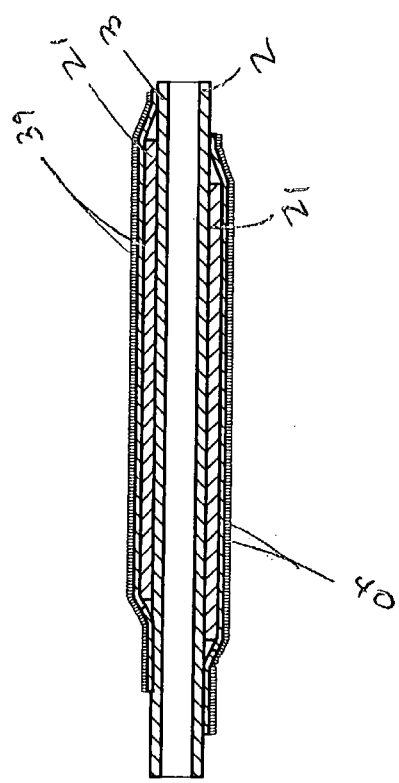
FIG. 9 is a cross-sectional view of the orthopedic device of FIG. 2 for stabilizing the thumb.

The thumb support can be worn on either the right or left hand, as shown in FIGS. 3-5. In use, the user inserts his or her thumb into the extended elements (14, 15) through the thumb opening 19 such that the hand is in the hand opening 20. The user would then releaseably secure the tab 34 to the mating portion 35 and then wrap the wrist strap 30 around the wrist, adjusting compression, and releaseably securing the wrist strap to itself. The user may also wrap the thumb strap 36 around the extended elements (14, 15) about adjacent to the distal edges (6, 10) of the first sheet 2 and second sheet 3 and releaseably secure the thumb strap to itself. One or more stay members 21 may be inserted into each elongated sleeve (26, 27) either prior to or after the thumb support is releaseably secured to the hand and wrist of a user. In the preferred embodiment, the thumb support comprises at least one stay member 21 in each elongated sleeve (26, 27).

The thumb support stabilizes the thumb generally as a result of the tension of the wrist strap with the first and second sheets and the extended elements. In embodiments wherein the thumb support comprises at least one stay member, preferably at least one stay member inserted in the first elongated sleeve and at least one stay member inserted in the second elongated sleeve, the strap envelops the bottom part of the stay members to offer further adjustability of the stabilization of the thumb and further thumb stabilizing. The wrist strap allows adjustment of tension against bottom portion of the stay members, offering adjustment to the stability of the stay members on the thumb to meet individual needs and comfort. The wrist strap further offers adjustment of tension around the wrist for individual needs and comfort.

The invention claimed is:

1. An orthopedic device for stabilizing the thumb comprising
    a) a first sheet having an outer surface, an inner surface, a right edge, a left edge, a distal edge and a lateral edge and a second sheet having an outer surface, an inner surface, a right edge, a left edge, a distal edge and a lateral edge with the right edge of the first sheet attached to the right edge of the second sheet;
    b) a first elongated sleeve on the outer surface of the first sheet and a second elongated sleeve on the outer surface of the second sheet, the first elongated sleeve defined by a piece of material secured at its periphery to the outer surface of the first sheet and the second elongated sleeve defined by a piece of material secured at its periphery to the outer surface of the second sheet, with the piece of material defining the first elongated sleeve comprising a slit for removeably inserting one or more stay members into the first elongated sleeve and the piece of material defining the second elongated sleeve comprising a slit for removeably inserting one or more stay members into the second elongated sleeve; and
    c) one or more stay members in the first elongated sleeve and/or second elongated sleeve wherein the stay members are made from a soft metal material and include a bend that is ergonomically shaped to follow the contour of a hand and a thumb of a user.

2. An orthopedic device for stabilizing the thumb comprising:
    a) a first sheet having an outer surface, an inner surface, a right edge, a left edge, a distal edge and a lateral edge and a second sheet having an outer surface, an inner surface, a right edge, a left edge, a distal edge and a lateral edge with the right edge of the first sheet attached to the right edge of the second sheet;
    b) a first elongated sleeve on the outer surface of the first sheet and a second elongated sleeve on the outer surface of the second sheet, the first elongated sleeve defined by a piece of material secured at its periphery to the outer surface of the first sheet and the second elongated sleeve defined by a piece of material secured at its periphery to the outer surface of the second sheet, with the piece of material defining the first elongated sleeve comprising a slit for removeably inserting one or more stay members into the first elongated sleeve and the piece of material defining the second elongated sleeve comprising a slit for removeably inserting one or more stay members into the second elongated sleeve; and
    c) one or more stay members in the first elongated sleeve and/or second elongated sleeve wherein the stay members are made from a soft metal material that is ergonomically shaped to follow the contour of a hand and a thumb of a user
    wherein the distal edge of the first sheet has a first extended element about adjacent to the right edge and a first arcuate section and the distal edge of the second sheet has a second extended element about adjacent to the right edge and a second arcuate section wherein the first arcuate section and the second arcuate section are attached together and the distal edge of the first sheet along a plane from the right edge to the first arcuate section and the distal edge of the second sheet along a plane from the right edge to the second arcuate section define a thumb opening.

3. An orthopedic device of claim 1 wherein the first sheet and second sheet are made from an open cell urethane foam.

4. An orthopedic device for stabilizing the thumb comprising:
    a) a first sheet having an outer surface, an inner surface, a right edge, a left edge, a distal edge and a lateral edge and a second sheet having an outer surface, an inner surface, a right edge, a left edge, a distal edge and a lateral edge with the right edge of the first sheet attached to the right edge of the second sheet;
    b) a first elongated sleeve on the outer surface of the first sheet and a second elongated sleeve on the outer surface of the second sheet, the first elongated sleeve defined by a piece of material secured at its periphery to the outer surface of the first sheet and the second elongated sleeve defined by a piece of material secured at its periphery to the outer surface of the second sheet, with the piece of material defining the first elongated sleeve comprising a slit for removeably inserting one or more stay members into the first elongated sleeve and the piece of material defining the second elongated sleeve comprising a slit for removeably inserting one or more stay members into the second elongated sleeve; and
    c) one or more stay members in the first elongated sleeve and/or second elongated sleeve wherein the stay members are made from a soft metal material that is ergonomically shaped to follow the contour of a hand and a thumb of a user wherein the right edge of the first sheet and the right edge of the second sheet are each curvilinear having an arch or kink at about the midpoint of the right edges of the first sheet and the second sheet such that the right edge of the first sheet and the right edge of the second sheet are shaped to substantially conform to the outer contour of the radial of the hand of a user from about the wrist to about distal joint of the thumb.

5. An orthopedic device for stabilizing the thumb comprising:
   a) a first sheet having an outer surface, an inner surface, a right edge, a left edge, a distal edge and a lateral edge and a second sheet having an outer surface, an inner surface, a right edge, a left edge, a distal edge and a lateral edge with the right edge of the first sheet attached to the right edge of the second sheet;
   b) a first elongated sleeve on the outer surface of the first sheet and a second elongated sleeve on the outer surface of the second sheet, the first elongated sleeve defined by a piece of material secured at its periphery to the outer surface of the first sheet and the second elongated sleeve defined by a piece of material secured at its periphery to the outer surface of the second sheet, with the piece of material defining the first elongated sleeve comprising a slit for removeably inserting one or more stay members into the first elongated sleeve and the piece of material defining the second elongated sleeve comprising a slit for removeably inserting one or more stay members into the second elongated sleeve; and
   c) one or more stay members in the first elongated sleeve and/or second elongated sleeve wherein the stay members are made from a soft metal material that is ergonomically shaped to follow the contour of a hand and a thumb of a user
   wherein the distal edge of the first sheet substantially along a plane from the first arcuate section to the lateral edge of the first sheet, the distal edge of the second sheet substantially along a plane from the second arcuate section to the lateral edge of the second sheet, the lateral edge of the first sheet and lateral edge of the second sheet define a hand opening such that the orthopedic device is substantially in the form of an open sleeve that can be worn on and releaseably secured to either the right hand or left hand of a user.

6. An orthopedic device for stabilizing the thumb comprising:
   a) a first sheet having an outer surface, an inner surface, a right edge, a left edge, a distal edge and a lateral edge and a second sheet having an outer surface, an inner surface, a right edge, a left edge, a distal edge and a lateral edge with the right edge of the first sheet attached to the right edge of the second sheet;
   b) a first elongated sleeve on the outer surface of the first sheet and a second elongated sleeve on the outer surface of the second sheet, the first elongated sleeve defined by a piece of material secured at its periphery to the outer surface of the first sheet and the second elongated sleeve defined by a piece of material secured at its periphery to the outer surface of the second sheet, with the piece of material defining the first elongated sleeve comprising a slit for removeably inserting one or more stay members into the first elongated sleeve and the piece of material defining the second elongated sleeve comprising a slit for removeably inserting one or more stay members into the second elongated sleeve; and
   c) one or more stay members in the first elongated sleeve and/or second elongated sleeve wherein the stay members are made from a soft metal material that is ergonomically shaped to follow the contour of a hand and a thumb of a user
   d) a wrist strap having a first end and a second end, the wrist strap being attached on the first end to the left edge of the second sheet and the second end to a wrist strap securing portion.

7. An orthopedic device of claim 6 wherein the first end of the wrist strap is attached to the left edge of the second sheet by third attachment means selected from the group consisting of Radio Frequency welding, stitching, adhesives and combinations thereof.

8. An orthopedic device of claim 6 wherein the wrist strap is made from hook engagable material and the wrist strap securing portion comprises the hook portion of a hook and loop type fastener.

9. An orthopedic device of claim 6 further comprising a tab made from the hook portion of a hook and loop type fastener having a first end and a second end with the tab being attached at the first end to the left edge of the second sheet and a mating portion made from the loop portion of a hook and loop type fastener is attached to the outer surface of the first sheet about adjacent to the elongated sleeve and left edge of the first sheet.

10. An orthopedic support of claim 9 where the first end of the tab is attached to the left edge of the second sheet by third attachment means selected from the group consisting of Radio Frequency welding, stitching, adhesives and combinations thereof.

11. An orthopedic device for stabilizing the thumb comprising:
   a) a first sheet having an outer surface, an inner surface, a right edge, a left edge, a distal edge and a lateral edge and a second sheet having an outer surface, an inner surface, a right edge, a left edge, a distal edge and a lateral edge with the right edge of the first sheet attached to the right edge of the second sheet;
   b) a first elongated sleeve on the outer surface of the first sheet and a second elongated sleeve on the outer surface of the second sheet, the first elongated sleeve defined by a piece of material secured at its periphery to the outer surface of the first sheet and the second elongated sleeve defined by a piece of material secured at its periphery to the outer surface of the second sheet, with the piece of material defining the first elongated sleeve comprising a slit for removeably inserting one or more stay members into the first elongated sleeve and the piece of material defining the second elongated sleeve comprising a slit for removeably inserting one or more stay members into the second elongated sleeve;
   c) one or more stay members in the first elongated sleeve and/or second elongated sleeve wherein the stay members are made from a soft metal material that is ergonomically shaped to follow the contour of a hand and a thumb of a user; and
   d) a thumb strap having a first end and a second end and attached at the first end to the extended element on the outer surface of the second sheet and at the second end to a thumb strap securing portion.

12. An orthopedic device of claim 9 wherein the thumb strap is made from hook engagable material and the thumb strap securing portion is made from the hook portion of a hook and loop type fastener.

13. An orthopedic support of claim 12 wherein the first end of the thumb strap is attached to the extended element by fifth attachment means selected from the group consisting of Radio Frequency welding, stitching, adhesives and combinations thereof.

14. An orthopedic support of claim 1 wherein the right edge of the first sheet and right edge of the second sheet are attached together by first attachment means selected from the group consisting of Radio Frequency welding, stitching, adhesives and combinations thereof.

15. A method for stabilizing the thumb of a user comprising at least the steps of providing the orthopedic device of claim 1 and applying the orthopedic device of claim 1 to either the right hand or left hand of the user.

16. A method for stabilizing the thumb of a user comprising:
at least the steps of providing,
a) a first sheet having an outer surface, an inner surface, a right edge, a left edge, a distal edge and a lateral edge and a second sheet having an outer surface, an inner surface, a right edge, a left edge, a distal edge and a lateral edge with the right edge of the first sheet attached to the right edge of the second sheet;
b) a first elongated sleeve on the outer surface of the first sheet and a second elongated sleeve on the outer surface of the second sheet, the first elongated sleeve defined by a piece of material secured at its periphery to the outer surface of the first sheet and the second elongated sleeve defined by a piece of material secured at its periphery to the outer surface of the second sheet, with the piece of material defining the first elongated sleeve comprising a slit for removeably inserting one or more stay members into the first elongated sleeve and the piece of material defining the second elongated sleeve comprising a slit for removeably inserting one or more stay members into the second elongated sleeve
c) one or more stay members in the first elongated sleeve and/or second elongated sleeve wherein the stay members are made from a soft metal material that is ergonomically shaped to follow the contour of a hand and a thumb of a user
d) a wrist strap having a first end and a second end, the wrist strap being attached on the first end to the left edge of the second sheet and the second end to a wrist strap securing portion; and
e) a tab made from the hook portion of a hook and loop type fastener having a first end and a second end with the tab being attached at the first end to the left edge of the second sheet and a mating portion made from the loop portion of a hook and loop type fastener is attached to the outer surface of the first sheet about adjacent to the elongated sleeve and left edge of the first sheet; and
having the hand of the user in the hand opening, releaseably securing the tab to the mating portion, wrapping the wrist strap around the wrist, adjusting compression, releaseably securing the wrist strap to itself and inserting one or more stay members into the elongated sleeves.

17. A method for stabilizing the thumb of a user comprising the steps of providing the orthopedic device of claim 11, inserting the thumb of a user into the extended element of the first sheet and the extended element of the second sheet and through the thumb opening such that the hand of the user is in the hand opening, wrapping the thumb strap around the extended element of the first sheet and the extended element of the second sheet about adjacent to the distal edge of the first sheet and the distal edge of the second sheet, releaseably securing the thumb strap to itself and inserting one or more stay members into the elongated sleeves.

18. An orthopedic device for stabilizing a thumb of a wearer relative to the wearer's wrist and hand, said thumb stabilizer comprising:
a) a sleeve including at least one sheet of material defining a wrist portion for extending at least partially over the wearer's wrist, a hand portion for extending at least partially over the wearer's hand, and a thumb portion for extending over at least two sides of the thumb; and
b) at least two stays wherein one of the stays is adapted to be coupled to the thumb and hand portions of the sleeve on one of the sides of the thumb and wherein another one of the stays is adapted to be coupled to the thumb and hand portions of the sleeve on another side of the thumb.

19. An orthopedic device of claim 18 wherein the thumb portion of the sleeve extends over two opposite sides of the thumb and wherein the two stays extend over opposite sides of the thumb on opposite sides of the thumb portion.

20. An orthopedic device of claim 19, wherein the thumb portion of the sleeve extends over palmar and dorsal sides of the thumb and wherein the two stays extend over palmar and dorsal sides of the thumb.

21. An orthopedic device of claim 18, wherein the thumb portion extends around at least a base of the thumb.

22. An orthopedic device of claim 21, wherein the thumb portion defines an opening through which a top portion of the thumb extends.

23. An orthopedic device of claim 22, further comprising a pair of stay pockets extending from the hand portion of the sleeve onto the thumb portion of the sleeve, each of the stay pockets holding a respective one of the stays on the respective side of the thumb portion.

24. An orthopedic device of claim 23, further comprising a thumb strap extending over ends of the stays and the thumb portion, and encircling the wearer's thumb.

25. An orthopedic device of claim 24, further comprising a wrist strap extending over the wrist portion of the sleeve and encircling the wearer's wrist.

26. An orthopedic device of claim 18, wherein the stays are constructed of a malleable material.

27. An orthopedic device of claim 26, wherein the stays each include one kink positioned to correspond to curvature of a base of the wearer's thumb.

28. An orthopedic device of claim 18, wherein the sleeve is reversible so as to have portions extending over opposite sides of the wearer's wrist, hand and thumb thereby reversing sides of the thumb on which the stays are positions.

29. An orthopedic device for stabilizing a thumb of a wearer comprising:
a sheet configured to enclose at least portions of the hand of the wearer, wherein the sheet includes an extended element configured to extend distally along at least past a proximal joint of, and circumferentially around at least a portion of the thumb; and
an adjustable thumb strap having a first end and a second end, the first end of the thumb strap attached to the extended thumb element and the second end of the thumb strap including a securing portion, wherein the adjustable thumb strap is configured to be extended and secured around the thumb element so as to provide support for the thumb.

30. An orthopedic device of claim 29, wherein the securing portion of the adjustable thumb strap is configured to attach to a portion of the thumb strap.

31. An orthopedic device of claim 29, wherein the extended element is configured to extend from a lateral edge of the sheet proximate to a wrist of the wearer to a distal edge of the sheet proximate to a distal joint of the thumb, and wherein the first end of the thumb strap is attached proximate to the distal edge.

32. An orthopedic device of claim 31, further comprising a wrist strap having a first end attached proximate to the lateral edge of the sheet and a second end attached to a securing portion, wherein the wrist strap is configured to be extended and secured around the wrist.

33. An orthopedic device of claim 32, further comprising at least one stay member having a proximal end and a distal end, the stay member coupled to the sheet and configured to extend at least along the hand at the proximal end and the thumb at the distal end, wherein the distal end is configured to extend under the thumb strap when the thumb strap is secured around the thumb element.

34. An orthopedic device of claim 33, wherein the proximal end of the stay member is configured to extend under the secured wrist strap.

35. An orthopedic device of claim 33, wherein the distal end of the stay member extends proximate to a distal joint of the thumb.

36. An orthopedic device of claim 33, wherein the stay member includes a contour configured to extend along the wrist, hand, and thumb.

37. An orthopedic device of claim 36, wherein the contour of the stay member includes an arch positioned between the proximal and distal ends and configured to substantially conform to a contour of the hand and thumb.

38. An orthopedic device of claim 33, wherein the stay member is formed of a malleable material.

39. An orthopedic device of claim 33, wherein the stay member is coupled to the sheet by an elongated sleeve.

40. An orthopedic device of claim 33, further comprising a second stay member.

41. An orthopedic device of claim 32, wherein the wrist strap is constructed of a hook-engageable material.

42. An orthopedic device of claim 29, wherein the thumb strap is constructed of a hook-engageable material.

43. An orthopedic device of claim 29, wherein the sheet terminates short of covering a palm of the hand and defines a hand opening so as to promote use on a right or a left hand.

44. An orthopedic device of claim 29, wherein at least a portion of the extended element is completely and securely closed about its periphery.

45. An orthopedic device for stabilizing a thumb of a wearer comprising:
   a sheet configured to enclose at least portions of the hand of the wearer, the sheet extending distally from a lateral edge proximate to a wrist to a distal edge proximate to a distal joint of the thumb, wherein a portion of the sheet is configured to extend along a substantial portion of the thumb, and about the thumb, at least to a distal joint of the thumb; and
   at least one stay member coupled to the sheet and having a proximal end and a distal end, wherein the stay member is configured to extend at least along the hand at the proximal end and proximate to the distal joint of the thumb at the distal end to provide support for the thumb.

46. An orthopedic device of claim 45, wherein the stay member includes a contour configured to extend along the wrist, hand, and thumb.

47. An orthopedic device of claim 46, wherein the contour of the stay member includes an arch positioned between the proximal and distal ends and configured to substantially conform to a contour of the hand and thumb.

48. An orthopedic device of claim 45, wherein the stay member is formed of a malleable material.

49. An orthopedic device of claim 45, wherein the stay member is coupled to the sheet by an elongated sleeve.

50. An orthopedic device of claim 45, further comprising an adjustable thumb strap configured to extend around the extended element and a wrist strap configured to extend around the wrist, wherein the proximal end of the stay member is configured to extend under the wrist strap and the distal end of the stay member is configured to extend under the thumb strap.

51. An orthopedic device of claim 45, further comprising a second stay member.

52. An orthopedic device of claim 49, wherein the elongated sleeve comprises a slit proximate to the lateral edge of the sheet to allow insertion of the stay member therein.

53. An orthopedic device of claim 45, wherein at least a portion of the sheet of material extends circumferentially to completely enclose the thumb about its periphery.

* * * * *

UNITED STATES PATENT AND TRADEMARK OFFICE
CERTIFICATE OF CORRECTION

| | | |
|---|---|---|
| PATENT NO. | : 8,657,771 B2 | Page 1 of 1 |
| APPLICATION NO. | : 10/409308 | |
| DATED | : February 25, 2014 | |
| INVENTOR(S) | : Edward Weaver et al. | |

It is certified that error appears in the above-identified patent and that said Letters Patent is hereby corrected as shown below:

In the Specification

Column 2
Line 64, delete "hypercell" and insert -- hypercel --, therefor.

In the Claims

Column 7
Line 8, in claim 4, delete "distal" and insert -- metacarpophalangeal --, therefor.

Column 10
Line 51, in claim 29, delete "of" and insert -- of, --, therefor.

Signed and Sealed this
Seventeenth Day of February, 2015

Michelle K. Lee
*Deputy Director of the United States Patent and Trademark Office*